(12) United States Patent
Belalcazar et al.

(10) Patent No.: US 7,860,567 B2
(45) Date of Patent: Dec. 28, 2010

(54) SENSOR FOR EDEMA (75) Inventors: Andres Belalcazar, St. Paul, MN (US);
Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 436 days.

(21) Appl. No.: 11/469,018

(22) Filed: Aug. 31, 2006

(65) Prior Publication Data
US 2008/0058885 A1 Mar. 6, 2008

(51) Int. Cl.
*A61N 1/08* (2006.01)
(52) U.S. Cl. .............................. 607/17; 600/508; 607/34
(58) Field of Classification Search ................. 600/508, 600/510, 542; 607/17, 18, 20, 42, 34, 35
See application file for complete search history.

(56) References Cited

U.S. PATENT DOCUMENTS

| | | | |
|---|---|---|---|
| 5,876,353 A * | 3/1999 | Riff | 607/9 |
| 6,076,015 A | 6/2000 | Hartley et al. | |
| 6,266,564 B1 | 7/2001 | Hill et al. | |
| 6,438,408 B1 * | 8/2002 | Mulligan et al. | 600/510 |
| 6,629,951 B2 * | 10/2003 | Laufer et al. | 607/96 |
| 2004/0134496 A1 | 7/2004 | Cho et al. | |
| 2005/0182342 A1 | 8/2005 | Dinsmoor et al. | |
| 2005/0288722 A1 | 12/2005 | Eigler et al. | |
| 2006/0037617 A1 | 2/2006 | Walke | |
| 2006/0064134 A1 | 3/2006 | Mazar et al. | |
| 2006/0074453 A1 * | 4/2006 | Kieval et al. | 607/9 |
| 2006/0241711 A1 * | 10/2006 | Sathaye | 607/28 |
| 2007/0142727 A1 | 6/2007 | Zhang et al. | |
| 2007/0249950 A1 | 10/2007 | Piaget et al. | |

FOREIGN PATENT DOCUMENTS

EP 0702977 A2 3/1996

OTHER PUBLICATIONS

Hauck, R. W., et al., "Implantation of Accuflex and Strecker stents in malignant bronchial stenoses by flexible bronchoscopy", *Chest*, 112(1), (Jul. 1997),134-144.

McNamee, J. E., et al., "Peribronchial electrical admittance measures lung edema and congestion in the dog", *J Appl Physiol.*, 49(2), (Aug. 1980), 337-341.

Piaget, Thomas, et al., "Implanted Air Passage Sensors", U.S. Appl. No. 11/379,396, filed Apr. 20, 2006, 28 pages.

(Continued)

*Primary Examiner*—Scott M Getzow
*Assistant Examiner*—Joseph M Dietrich
(74) *Attorney, Agent, or Firm*—Schwegman, Lundberg & Woessner, P.A.

(57) ABSTRACT

A sensor is located within the body of a subject, such as for capturing pacing pulses transmitted as part of cardiac therapy from an implanted cardiac function management device. Counted pulses may be used to derive the onset of pulmonary edema within the body through pulse characteristics such as frequency and amplitude. The sensor may be anchored within mediastinal pleura or the airway of the body with the ability to communicate wirelessly to one or more other medical devices, such as an implanted cardiac function management device. It may also adjust transmission of the communication to discriminate among multiple sensors. Methods of use are also described.

30 Claims, 4 Drawing Sheets

OTHER PUBLICATIONS

"U.S. Appl. No. 11/379,396, Non-Final Office Action mailed Feb. 4, 2009", 15 pgs.

"U.S. Appl. No. 11/379,396, Response filed May 4, 2009 to Non Final Office Action mailed Feb. 4, 2009", 10 pgs.

"U.S. Appl. No. 11/379,396, Non-Final Office Action mailed Aug. 21, 2009", 16 pgs.

"U.S. Appl. No. 11/379,396, Notice of Allowance mailed Feb. 19, 2010", 9 pgs.

"U.S. Appl. No. 11/379,396, Preliminary Amendment filed Jun. 9, 2006", 8 pgs.

"U.S. Appl. No. 11/379,396, Response filed Nov. 23, 2009 to Non Final Office Action mailed Aug. 21, 2009", 14 pgs.

* cited by examiner

SENSOR FOR EDEMA

TECHNICAL FIELD

This patent document pertains generally to implantable medical devices, and more particularly, but not by way of limitation, to an implantable fluid sensor.

BACKGROUND

Physiological conditions of a subject can provide useful information about the subject's health status, such as to a physician or other caregiver. Devices may be implanted within a patient's body for monitoring certain physiological conditions. Cardiovascular monitoring or function management devices include pacemakers, cardioverters, defibrillators, cardiac resynchronization therapy (CRT), drug delivery or combinations of the above. Implantable pacers are devices capable of delivering higher energy electrical stimuli to the heart. A defibrillator is capable of delivering a high-energy electrical stimulus via leads that is sometimes referred to as a defibrillation shock. The shock interrupts a fibrillation, allowing the heart to reestablish a normal rhythm for efficient pumping of blood. These systems are able to sense cardiac signals and deliver therapy to the heart based on such signals. Additionally, the arrangement of the leads of such systems in the body allows for other physiologic signals to be sensed.

Variations in how much fluid is present in a subject's thoracic region can take various forms and can be an indication of other health concerns such as heart failure. As one example, eating salty foods can result in the retainment of excessive fluid in the thorax, which is commonly referred to as "thoracic fluid," and elsewhere. Another source of fluid build-up in the thorax is pulmonary edema, which involves a build-up of extravascular fluid in or around the lungs.

One cause of pulmonary edema is congestive heart failure (referred to as "CHF"), which is also sometimes referred to as "chronic heart failure," or simply as "heart failure." CHF may be conceptualized as an enlarged weakened heart muscle. The impaired heart muscle results in poor cardiac output of blood. As a result of such poor blood circulation, blood tends to pool in blood vessels in the lungs and becomes a barrier to normal oxygen exchange. In brief, pulmonary edema may be an indicative and important condition associated with CHF.

Pulmonary edema, if it exists, may present a medical emergency that requires immediate care. While it can sometimes prove fatal, the outlook for subjects possessing pulmonary edema can be good upon early detection and prompt treatment. If left undetected (and consequently untreated), pulmonary edema may lead to death. Thus there is a need for a device and method to measure the accumulation of fluid in the lungs of a subject with early indication and low power consumption.

SUMMARY

This document describes, among other things, certain examples in which a sensor is implanted within the subject's body, such as for collecting energy from paced pulses transmitted by a cardiac function management device (CFMD), such as a separate pulse generator (PG), cardiac resynchronization therapy (CRT), implantable cardiac device (ICD) located elsewhere in the same subject. In such an example, the collected energy may be stored in the sensor, as well as used to communicate information collected over time. The sensor may additionally or alternatively detect one or more physiological parameters, or co-exist with other sensors within the body. The sensor may be anchored within a person's mediastinal pleura or within the airway and may be able to communicate information wirelessly to one or more other implantable or other medical devices.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. A number of embodiments may describe location of the sensor apparatus within the airway of a subject's body, however it is perceived that other locations are within the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In general, edema (i.e., an excess of fluid build-up in a region of a subject) is a failure of decompensation of one or more homeostatic processes within a subject's body. The body normally prevents or alleviates build-up of excess fluids by maintaining adequate pressures and concentrations of salt and protein. If a disease of the body affects any of these bodily mechanisms or the mechanisms are unable to react efficiently, the result may be edema, such as pulmonary edema. There are several conditions or diseases that may cause or affect pulmonary edema. These may include, among others, heart failure, left-sided myocardial infarction, high blood pressure, altitude sickness, emphysema, cancers that affect the lymphatic system, diseases that disrupt protein concentrations, or epithelial pathologies, such as those caused by inhalation of toxic chemicals, leading to flooding of the alveoli.

While pulmonary edema may be a sign of many conditions or diseases, the prospect that pulmonary edema may be a sign of failing heart circulation is often of first concern to caregivers (e.g., health care professionals) due to the severity of its nature. Congestive heart failure (CHF) is one example which may be conceptualized as an enlarged weakened heart muscle. The impaired heart muscle results in poor blood circulation and becomes a barrier to normal oxygen exchange in the body. Such conditions can be difficult to diagnose early for prompt treatment. Unfortunately, the first indication that an attending caregiver typically has of an occurrence of pulmonary edema is very late in the disease process, such as when it becomes a physical manifestation with swelling, noticeable weight gains, jugular venous distension, or breathing difficulties so overwhelming as to be noticed by the subject, prompting a visit to his/her caregiver. For a heart failure subject, hospitalization at such a (physically apparent) time would likely be required.

Morbidity and mortality of heart failure can potentially be lowered with timely detection and appropriate treatment of disease conditions in their early stages, such as upon early detection and treatment of pulmonary edema. Early detection and treatment of pulmonary edema may reduce or eliminate the need for hospital admission of subjects with heart failure in addition to shortening recovery time. A reduction or elimination of the need for hospitalization results in lower health care costs.

Figure 1:
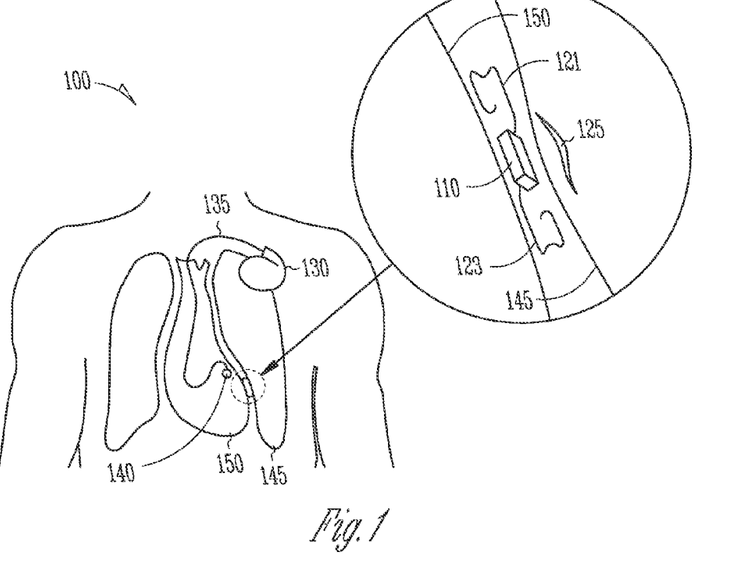
FIG. 1 illustrates a particular example of a sensor located within the mediastinal pleura region of a human body.

Detecting early signs of pulmonary edema may be most effective in the bronchial region of the lungs, where the buildup of fluid begins prior to spreading elsewhere within the lung tissue. The term "peribronchial cuffing" refers to acute pulmonary edema caused by excess fluid content in the tissue surrounding the bronchial wall as well as the peribronchial interstitial space. In certain examples, implanting a physiological sensor in a bronchus of the lung or within the thin membrane that lines the chest cavity in the area between the lungs, known as the mediastinal pleura, can provide early detection of excess fluid formation. FIG. 1 illustrates generally, by way of example, but not by limitation, one example of portions of a system 100 to detect a pacing pulse or other external parameter from within the body of a subject. A sensor 110 is shown in the example of FIG. 1 as positioned within the mediastinal pleura region between the heart 150 and left lung 145. In this example, the system 100 comprises the sensor 110, having electrodes 121 and 123 extending therefrom for accumulation or transfer of energy between the sensor 110 and a separate and unattached CFMD 130. The information transferred between the CFMD 130 and the sensor 110 may provide characteristics which indicate a concentration of tissue fluid 125 accumulation. It is anticipated that the energy accumulated or transferred by the sensor 110 be in various forms which include, but are not limited to, sine waves and non-sinusoidal pulses. In certain examples, the pacing signals from the CFMD 130, as communicated by electrode 140 via lead wire 135, may be picked up by electrodes 121 and 123. The magnitude of the signals or the number of pulses within a given time period may indicate tissue fluid 125 concentration. In certain examples, an increase in signal magnitude may indicate increased tissue fluid 125 accumulation. In certain examples, an increase in the number of pacing pulses within a given time may indicate an increase in tissue fluid 125 accumulation. The determination of tissue fluid accumulation may be accomplished by a separate an unattached medical device such as the CFMD 130 or a programmer which is not implanted in the body. However, it is within the scope of the present invention that the determination of tissue fluid accumulation be made at the sensor 110.

Figure 2:
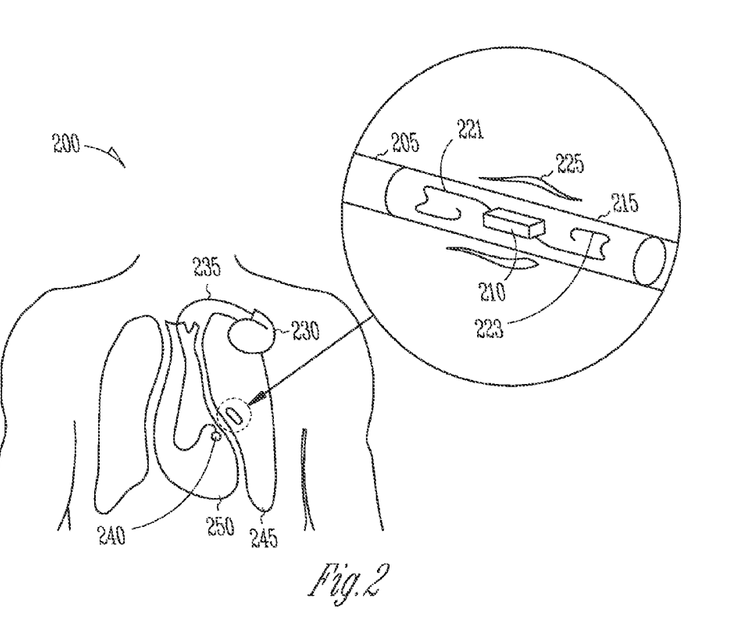
FIG. 2 illustrates a particular example of a sensor within the human respiratory system.

FIG. 2 illustrates one example of portions of a system 200 to detect a pacing pulse or other external parameter from within the body of a subject. A sensor 210 is shown in the example of FIG. 2 as attached to a stent 215, which is disposed or residing within an airway 205, such as a bronchi of left lung 245, or other similar region of the respiratory system. In this example, the system 200 comprises the sensor 210, having electrodes 221 and 223 extending therefrom for accumulation or transfer of energy between the sensor 210 and a separate and unattached CFMD 230. The characteristics of the information transferred between the CFMD 230 and the sensor 210 may indicate the amount of tissue fluid 225 accumulation in the monitored region. In certain examples, a decrease in signal magnitude or pulse frequency may indicate an increase in tissue fluid 225 accumulation.

While a system including an implantable tissue fluid sensor that is communicatively coupled to an IMD is specifically discussed below as an illustrative example, the present systems and methods are not so limited. In FIG. 2, a CFMD 230 is implanted within the body of a subject. In this example, the CFMD 230 is connected to an electrode 240 attached by lead wire 235 which extends into or over the heart 250. In certain examples, the sensor 210 will require an energy source in order to operate separately and unattached to other devices. In certain examples the sensor 210 uses an energy source, such as a battery, but will have a limited duration and requires replacement or recharging by various methods. An alternative to this would be a device which enables the sensor 210 to collect energy from other sources within the subject's body. In certain examples, the sensor 210 includes the capability to collect energy that is transmitted or delivered by the pacing pulses of a CFMD 230 and to store the captured energy for sensor 210 operation. It is anticipated that the collection of energy may be combined with an energy storage for even greater energy capture.

Figure 3:
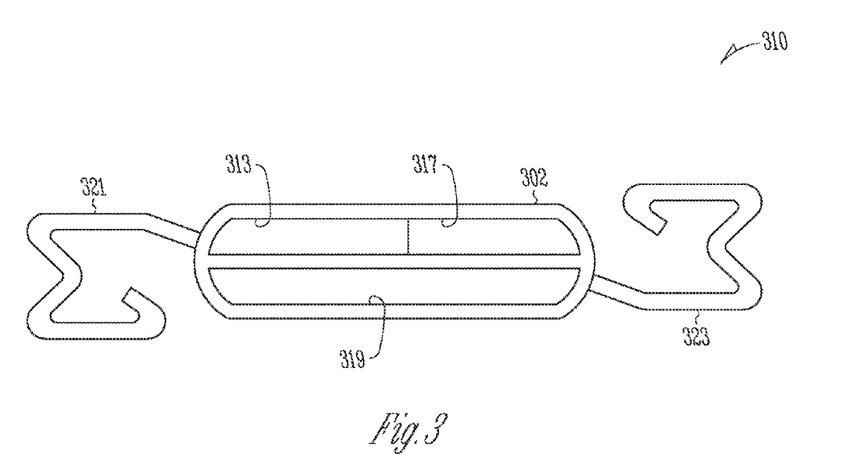
FIG. 3 illustrates one example of a sensor having a detector, an energy storage source and an energy collection circuit.

FIG. 3 illustrates an example in which the sensor module 310 comprises a sealed housing 302 configured to enclose at least a portion of one or more of the components that make up the sensor module 310. The material for the sealed housing 302 may include a flexible or rigid biocompatible material that will withstand conditions of long-term exposure inside a body. In certain examples, the sensor module 310 includes a detector 313 used to detect pacing pulses, such as that transmitted by a separate and unattached CFMD 230 located near the sensor module 310, either within the body or at a location external to the body. In certain examples, the CFMD 230 is located within approximately two centimeters (cm) of the sensor module 310, or otherwise located so as to ensure adequate charging of an energy storage device 317. Electrodes 321 and 323 may be used by the detector 313 to detect pacing pulses for storage by energy storage device 317 and subsequently processed by the energy collection circuit 319. In certain examples, electrodes 321 and 323 may be used by the energy collection circuit 319 to transmit signals to another device as an indication of tissue fluid 225 accumulation. In certain examples, there may be more than one sensor module 310 located within the body of a subject. In such cases, the additional device(s) may provide individual delay capability, such as to adjust the timing of the communication signal in relation to the pacing pulses of the receiving device in order to differentiate each device. In certain examples, electrodes 321 and 323 may be used to for active fixation of the sensor module 310 within the mediastinal pleura region of the body.

Figure 4:
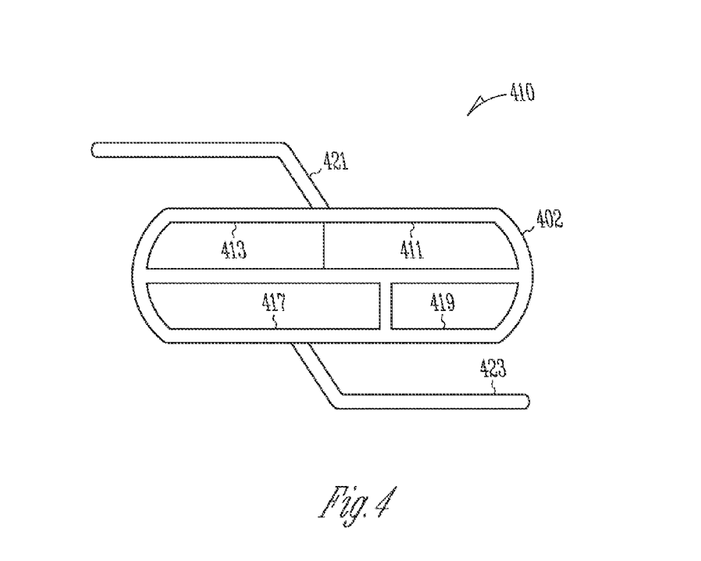
FIG. 4 illustrates one example of a sensor having a detector, a communication module, an energy storage source and an energy collection circuit.

FIG. 4 illustrates an example in which the sensor module 410 comprises a sealed housing 402 configured to enclose at least a portion of one or more of the components that make up the sensor module 410 similar to FIG. 3. In certain examples, the sensor module 410 includes a detector 413 used to detect pacing pulses which may be transmitted from a CFMD 230. Electrodes 421 and 423 may be used by an energy collection circuit 419 to collect or receive energy from a separate and unattached source such as pacing pulses from a CFMD 230 and store within an energy storage device 417, thus powering the energy collection circuit 419. A communication module 411 may allow the detector 413 to communicate information with another device, such as a CFMD 230 located near the sensor module 410, either within the body or at a location external to the body. In certain examples, the communication module 411 includes a processor (not shown), such as to direct energy collection and communication. In certain examples, the communication module 411 is further connected to the energy storage device 417 to obtain a source of power. In certain examples the energy storage device 417 includes capacitive storage capability such that it may be energized in a relatively short period of time and maintain the energy until needed by the communication module 411.

In certain examples, electrodes 421 and 423 may alternatively or additionally provide anchoring capability to fixate the sensor module 410 within the airway 205 through active or passive fixation. This can be practical, such as in the event a stent 215 is not used as part of the implant of the sensor module 410. In certain examples, the communication module 411 is configured to transmit information wirelessly, such as by use of an ultrasonic transmitter, an inductive transmitter, or a transmitter using the subject's body as a conductor. The communication module 411 may transmit information from the sensor module 410 to another location within the body, which need not be adjacent the sensor module 410, but instead can be remote from the sensor module 410. In such an example, the sensor module 410 may provide information used by a remotely implanted medical device as an input, such as to control delivery of energy or therapy to the subject. In certain examples, the communication module 411 is configured to use the subject's body as an electrical signal conductor to transmit information wirelessly. In certain examples, the communication module 411 is configured to transmit information acoustically within the subject's body. In certain examples, the communication module 411 transmits information wirelessly to a location outside the subject's body.

In certain examples, the energy collection circuit 419 may transmit signals to another device as an indication of tissue fluid 225 accumulation in or near the airway, which can be used, for example, to estimate the subject's onset of pulmonary edema. This information may then be communicated, such as by synchronizing a communication protocol with the pacing pulses of the CFMD 230, to communicate with the CFMD 230, or other receiving device. In certain examples, there may be more than one sensor module 410 located within an airway of the subject's respiratory system. In such cases, the additional device(s) may provide individual delay capability, such as to adjust the timing of the communication signal in relation to the pacing pulses of the CFMD 230. In this manner the separate delay times will enable the receiving device to differentiate, synchronize or discriminate between sensors.

Figure 5:
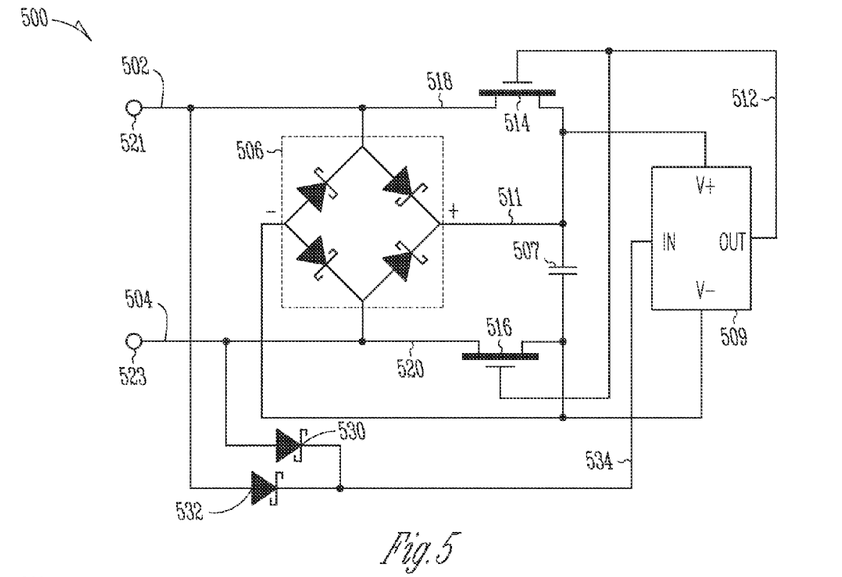
FIG. 5 is a schematic diagram of the energy collection circuit of FIG. 3.

FIG. 5 is a detailed schematic diagram of an apparatus 500, similar to the sensor module 310 of FIG. 3. The electrodes 521 and 523 are used with diode bridge 506 to detect energy from the pacing input pulse signals 502 and 504, or other similar signals. The input pulse signals 502 and 504 can be converted to a rectified signal 511 by diode bridge 506. This rectified signal 511 energizes charge capacitor 507, acting as an energy storage device. In certain examples, input pulse signals 502 and 504 comprise pacing pulses from an implanted medical device such as CFMD 130 in FIG. 1. In certain examples, a rechargeable battery may be used in the place of charge capacitor 507. Based upon the peak voltage and duration of the input pulse signals 502 and 504, the diode bridge 506 will allow capacitor 507 to charge sufficiently to exceed the minimum low supply voltage of accumulator 509. In certain examples, the accumulator 509 may include discrete components such as a counter and delay circuitry or may comprise a programmable logic device (PLD) designed to produce an output transition triggered by the accumulator input signal 534 reaching a threshold. In certain examples a voltage across capacitor 507 of at least three volts direct current (VDC) is used as the minimum low supply voltage of accumulator 509, acting as an energy collection circuit. The accumulator input signal 534 at the input (In) is carried through accumulator pulse diodes 530 and 532. When the accumulator input signal 534 reaches a threshold, accumulator 509 generates the toggle signal 512 at the output (Out), which may include an adjustable delay for discriminating the toggle signal 512 from other signals in the body such as CFMD 130. In certain examples, count pulse diodes 530 and 532 are standard Schottky diodes, however other devices capable of operating at low voltage with low voltage drop may be used. The toggle signal 512 will turn on switches 514 and 516, discharging the capacitor 507 thereby generating output pulse signals 518 and 520. In certain examples, the output pulse signals 518 and 520 are released into the body via electrodes 521 and 523, and may be detected by one or more sense amplifiers of a pulse generator associated with a CFMD 130, by any number of channels. In certain examples, this may include right atrium electrogram, left ventricle electrogram, right ventricle electrogram, or shock electrogram.

The amount of time for capacitor 507 to charge sufficiently to power accumulator counter 509 will be a function of the resistivity of the tissue surrounding the apparatus 500 and the tissues intervening between apparatus 500 and the source of the input pulse signals 502 and 504. In certain examples, resistivity in these tissues will permit more rapid charging of the capacitor 507, since the input pulse signals 502 and 504 appear as a lower impedance current source. Conversely, when the tissue resistivity is higher, the input pulse signals 502 and 504 will appear to have a higher impedance, so that the transfer of energy into apparatus 500 will be less efficient, requiring more input pulse signals 502 and 504 to sufficiently charge the capacitor 507. In certain examples, capacitor 507 is to be charged beyond the value of 1V, the electrodes of a sensing device can be placed within a tissue potential gradient of at least 1.5V. Such a magnitude will overcome voltage drops from the diodes of the rectifier bridge 506, having an approximate on-resistance of 200 ohms ($\Omega$). In certain examples, the current in apparatus 500 would be about 20 microamperes ($\mu$A), thus location of the source electrode, such as an LV electrode, between 1-5 cm from the electrodes 521 and 523 of apparatus 500 would be beneficial. In certain examples, a pacing pulse of 75 milliamps (mA) may be used having lead impedance of 600-1400Ω and voltages of 45-100V. In such examples, the increased voltage level would use a reduced pulse width of input pulse signals 502 and 504, such as to avoid evoking an unwanted heart contraction.

In certain examples, the measured voltage potential collected by apparatus 500 exceeds about 0.5 Volts (V) in order to bias the diode bridge 506, however typical pacing pulses have a maximum range of 7-10V and a pulse width of 500 microseconds (μs). In certain examples, a standard LV pulse could be delivered by the CFMD 130 with a value of 7V and a pulse width of 0.5 milliseconds (ms), and followed shortly thereafter (e.g. within 5 milliseconds) by a second LV pulse having a width of 100 ms. In certain examples, the input pulse signals 502 and 504 would have a value of 45-100V and a pulse width of approximately 25 μs. If for example capacitor 507 had a value of 0.22 microfarads, and input pulse signals 502 and 504 were 40-100V, having 25 μs pulse widths, approximately 387 pulses would be required to charge capacitor 507 to 1V. This would equate to approximately 5-10 minutes between capacitor 507 discharges, suitable for pulmonary edema monitoring. The human heart may be paced at these higher voltages but would need to have a narrower pulse width according to the inverse relationship known as the strength-duration curve. Using higher voltages (45-100V) will increase the complexity of the circuitry such as coupling a voltage multiplier and bi-phasic output circuitry to an electrode of the CFMD 130, such as the LV electrode. In certain examples, a different voltage-generating technique such as a flyback or boost converter may be used instead of a switched-capacitor voltage generator to achieve the higher voltage levels.

Figure 6:
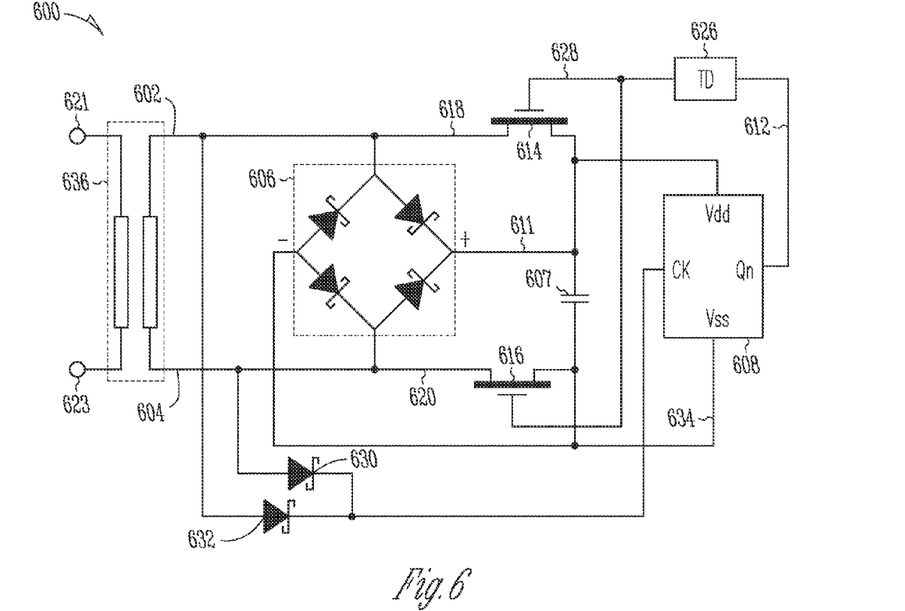
FIG. 6 is a schematic diagram of the energy collection circuit of FIG. 3, having a step-up transformer and time delay.

FIG. 6 is a detailed schematic diagram of an apparatus 600, similar to apparatus 500 of FIG. 5, with like elements numbered similarly. The apparatus 600 is used to collect pacing input pulses 602 and 604, or other similar signals collected at electrodes 621 and 623, and a transformer 636 steps up input voltages to a range of 1-7V, typically 0.2V at the electrodes 621 and 623. In certain examples, using a ratio of approximately 1:8 for transformer 636 would achieve the desired voltage of 1.5V but with reduced current by the same factor (8:1), thus requiring eight times the number of input pulses 602 and 604, as compared to using higher voltage pulses. In certain examples, collection of eight times the number of input pulses 602 and 604, over time, would take approximately one hour, which is sufficient for edema monitoring. The input pulses 602 and 604, after stepping up through transformer 636, can be converted to a rectified signal 611 by diode bridge 606. This rectified signal 611 energizes capacitor 607. When a minimum input threshold is met, counter 608 begins counting the count pulse 634 at the clock input (CK) of counter 608 as carried through count pulse diodes 630 and 632. When the specified number of the counter 608 is reached, its output (Qn) becomes active and a toggle signal 612 is generated, which may then be delayed by time delay 626, thus resulting in delayed toggle signal 628. This will ensure ventricular depolarization to occur following a pacing pulse used as input pulse signals 602 and 604 and allow the heart to become electrically silent. In certain examples, counter 608 is a seven stage, ripple-carry binary counter, although it is anticipated that various discrete components may be used alone or in conjunction with a PLD to achieve a similar result. In certain examples, time delay 626 uses a passive RC delay network, such as for a delay of 150-250 ms, although variations of type and style of the time delay is anticipated. After the time delay 626, switches 614 and 616 are turned on. This discharges the capacitor 607, thereby generating output pulses 618 and 620. In certain examples, the output pulses 618 and 620 are released into the body via electrodes 621 and 623, and may be detected by sense amplifiers of a pulse generator associated with a CFMD 130 by any number of channels. An advantage of time delay 626 is the improved ability of the sensing device to distinguish the output pulses 618 and 620 from other signals within the body. Although in this example the counter 608 and time delay 626 are shown as separate devices, it is anticipated that these can be combined or integrated as part of a PLD to achieve a similar result.

Figure 7:
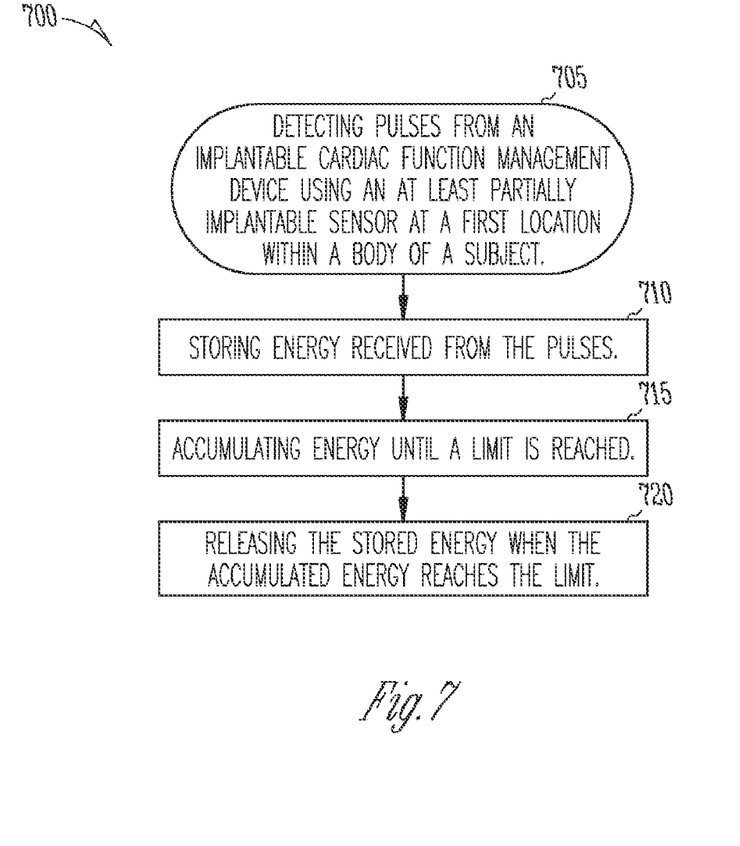
FIG. 7 is a is a flow diagram of an example of a method of detecting physiological parameters utilizing a sensor similar to that illustrated in FIGS. 1-4 and communicating with a cardiac function management device.

FIG. 7 is a is a flow diagram of a system 700 illustrating an example of a method of detecting physiological parameters utilizing a sensor similar to that illustrated in FIGS. 1 and 3 in communication with a cardiac function management device. At 705, a first sensed parameter is detected using an at least partially implantable sensor module at a first location within an airway of a subject's body. Examples of such parameters include a tissue fluid sensor for detection of early pulmonary edema. At 710, information about the first parameter is communicated from the first location to a second location that is outside the airway of the subject's body, such as by direct conductive connection or by wireless transmission. In certain examples, the wireless communication includes using an ultrasound signal, an inductive signal, or electrical signal communication using the body as an electrical signal conductor. In certain examples, at 715, an energy collection circuit collects energy received from a source that is outside of the sensor module and even possibly outside the airway. In certain examples, at 720, this collected energy may then be stored within an energy storage device within the sensor via capacitive charging. This stored energy may then be later used to power the detector within the sensor module or for transmission of information through the communication module to a separate location (such as by implanted cardiac function management or other implanted medical device at the separate location, for example).

It is to be understood that the above description is intended to be illustrative, and not restrictive. For example, the above-described embodiments (or aspects thereof) may be used in combination with each other. Other embodiments will be apparent to those of skill in the art upon reviewing the above description. For example, other forms of thoracic sensing can be used. These include, but are by no means limited to thoracic motion (e.g., due to respiration, heart beat or body movement), thoracic posture (e.g., due to upper body prone or bent with respect to lower body), thoracic pressure, thoracic sounds such as the lungs (e.g., crackle, cough, wheeze or rales) or the heart (e.g., first through fourth heart sounds, referred to as S1, S2, S3 or S4, or murmurs), thoracic voltage (thorax voltage such as heart electrocardiogram or muscle electromyogram) or transthoracic impedance (thorax impedance measurement).

The scope of the invention should, therefore, be determined with reference to the appended claims. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A system comprising:
a first device including a first electrode and a second electrode, at least a portion of which is adapted to reside in a body of a subject, wherein the first device is configured to measure a physiological first parameter, the first device including an energy collection unit coupled to the first and second electrodes; and
an implantable second device physically separate from and unattached to the first device, the second device configured to issue cardiac pacing pulses, wherein the energy collection unit of the first device is configured to aggregate energy collected from the cardiac pacing pulses by the first and second electrodes over two or more cardiac cycles, wherein the measurement of the physiological first parameter is a function of a quantity of the energy aggregated over the cardiac cycles.

2. The system of claim 1, in which the second device includes a cardiac function management device.

3. The system of claim 1, wherein the first device includes a communication module configured to transmit information about the first parameter via the first and second electrodes.

4. The system of claim 3, in which the communication module of the first device is configured to transmit information wirelessly, and comprises one or more of an ultrasonic transmitter, an inductive transmitter, and a body conductive transmitter.

5. The system of claim 4, in which the communication module is configured to transmit information synchronous to a pacing pulse delivered by the second device.

6. The system of claim 5, in which the communication module is configured to adjust transmission of information to permit communication from at least a third device separate from and unattached to the first device.

7. The system of claim 1, wherein the first device is sized and shaped to be fixated within the airway of a subject.

8. The system of claim 1, wherein the first device is sized and shaped to be fixated within the mediastinal pleura region of a subject.

9. The system of claim 1, wherein the first and second electrodes are configured to fixate at least a portion of the first device within the airway of a subject.

10. The system of claim 1, wherein the first and second electrodes are configured to fixate at least a portion of the first device within the mediastinal pleura region of a subject.

11. The system of claim 1, wherein the second device includes a lead, and wherein the first device is located approximately 2 cm from the lead of the second device.

12. The system of claim 1, wherein the first device is configured to capacitively store the energy collected from the cardiac pacing pulses.

13. The system of claim 1, wherein the first device is configured to measure a tissue fluid accumulation.

14. The system of claim 1, wherein the first device is configured to measure a tissue fluid accumulation as a function of the quantity of the energy aggregated over the cardiac cycles.

15. A method comprising:
collecting energy using first and second electrodes of a first device, the energy collected from cardiac pacing pulses issued from an implantable second device, the first device being at least partially implanted at a first location within a body of a subject, the first location being different from a location of the second device, wherein the second device is physically separate from and unattached to the first device;
aggregating the energy collected from the cardiac pacing pulses over two or more cardiac cycles using an energy collection unit of the first device, the energy collection unit coupled to the first and second electrodes; and
measuring a physiological first parameter as a function of a quantity of the energy aggregated over the cardiac cycles.

16. The method of claim 15, in which the collecting energy includes collecting energy from the cardiac pacing pulses issued from a cardiac function management device of the second device.

17. The method of claim 15, in which the collecting energy includes collecting energy using the first device located approximately 2 cm from a lead of the second device.

18. The method of claim 15, in which the measuring of the physiological first parameter includes measuring a tissue fluid accumulation.

19. The method of claim 15, in which the collecting energy includes capacitively storing the energy.

20. The method of claim 15, comprising counting cardiac pacing pulses delivered by the second device.

21. The method of claim 15, comprising wirelessly communicating with the second device.

22. The method of claim 21, in which the wirelessly communicating includes one or more of acoustic communication, inductive communication, and communication using the body as an electrical signal conductor.

23. A system comprising:
means for collecting energy using a first device, the energy collected from cardiac pacing pulses issued from an implantable second device, the first device being at least partially implanted at a first location within a body of a subject, the first location being different from a location of the second device, wherein the second device is physically separate from and unattached to the first device;
means for aggregating the energy collected from the cardiac pacing pulses over two or more cardiac cycles; and means for measuring a physiological first parameter as a function of a quantity of the energy aggregated over the cardiac cycles.

24. The system of claim 23, wherein the second device includes a cardiac function management device.

25. The system of claim 23, wherein the first device is located approximately 2 cm from a lead of the second device.

26. The system of claim 23, wherein the means for measuring the physiological first parameter is configured to measure a tissue fluid accumulation.

27. The system of claim 23, wherein the means for collecting energy includes means for capacitively storing energy.

28. The system of claim 23, comprising means for counting cardiac pacing pulses delivered by the second device.

29. The system of claim 23, comprising means for wirelessly communicating with the second device.

30. The system of claim 29, wherein the means for wirelessly communicating is configured to use one or more of acoustic communication, inductive communication, and communication using the body as an electrical signal conductor.

* * * * *